United States Patent
Wald et al.

(10) Patent No.: US 11,468,994 B2
(45) Date of Patent: Oct. 11, 2022

(54) PNEUMONIA READMISSION PREVENTION

(71) Applicant: CERNER INNOVATION, INC., Kansas City, KS (US)

(72) Inventors: Randall Wald, Kansas City, MO (US); Andrew Roberts, Overland Park, KS (US); Sasanka Are, Kansas City, MO (US)

(73) Assignee: CERNER INNOVATION, INC., North Kansas City, MO (US)

( * ) Notice: Subject to any disclaimer, the term of this patent is extended or adjusted under 35 U.S.C. 154(b) by 588 days.

(21) Appl. No.: 16/457,082

(22) Filed: Jun. 28, 2019

(65) Prior Publication Data

US 2020/0411193 A1    Dec. 31, 2020

(51) Int. Cl.
| | |
|---|---|
| *G16H 50/30* | (2018.01) |
| *G16H 10/60* | (2018.01) |
| *G06N 20/20* | (2019.01) |
| *G16H 50/20* | (2018.01) |
| *A61B 5/00* | (2006.01) |

(52) U.S. Cl.
CPC ............ *G16H 50/30* (2018.01); *G06N 20/20* (2019.01); *G16H 10/60* (2018.01); *A61B 5/4094* (2013.01); *A61B 5/7275* (2013.01); *G16H 50/20* (2018.01)

(58) Field of Classification Search
CPC ........ G16H 50/30; G16H 10/60; G16H 20/20; G16H 50/20; A61B 5/4094; A61B 5/7275
USPC .......................................................... 705/2
See application file for complete search history.

(56) References Cited

U.S. PATENT DOCUMENTS

| | | | | |
|---|---|---|---|---|
| 9,238,841 | B2 * | 1/2016 | Wong | G01N 33/68 |
| 9,267,175 | B2 * | 2/2016 | Wong | C12Q 1/6883 |
| 10,815,526 | B2 * | 10/2020 | Lindsell | C12Q 1/6883 |
| 2011/0313788 | A1 * | 12/2011 | Amland | G16Z 99/00 |
| | | | | 705/3 |
| 2012/0046965 | A1 * | 2/2012 | Ryan | G16H 50/30 |
| | | | | 705/2 |
| 2015/0227681 | A1 * | 8/2015 | Courchesne | G16B 25/10 |
| | | | | 506/9 |
| 2017/0206327 | A1 * | 7/2017 | Heywood | A61B 5/4833 |
| 2020/0143278 | A1 * | 5/2020 | Narain | G16H 50/70 |
| 2020/0191792 | A1 * | 6/2020 | Yu | G06N 20/20 |

* cited by examiner

Primary Examiner — Michael Tomaszewski
Assistant Examiner — Rachael Sojin Stone
(74) Attorney, Agent, or Firm — Shook, Hardy & Bacon L.L.P.

(57) ABSTRACT

A decision support tool is provided for discharging a patient by predicting the probability of a patient's readmission with pneumonia based on information available prior to discharge. The information used to make the prediction may include labs, vitals, diagnoses, and medications from prior encounters and from the current encounter. At least some of this information may be used to compute one or more severity metrics for the patient, such as a cancer score, an epilepsy or seizure score, a pneumococcal pneumonia score, and an instability score, to be input into one or more prediction models. An ensemble of machine learning models may be applied to the patient information to generate a prediction of that patient being readmitted with pneumonia within a future time interval. Based on the prediction, one or more intervening actions may be initiated to reduce the probability of readmission.

20 Claims, 10 Drawing Sheets

300

| HUMAN NAME | CODE NAME |
|---|---|
| Other Upper Respiratory Infection, Current | curr.diag..Other.upper.respiratory.infections |
| Non-Ionic Iodinated Contrast Media, Current | curr.med..non.ionic.iodinated.contrast.media |
| Viral Vaccines, Current | curr.med..viral.vaccines |
| Chronic Ulcer of Skin | diag..Chronic.ulcer.of.skin..199.. |
| Gout and Other Crystal Arthropathies | diag..Gout.and.other.crystal.arthropathies..54.. |
| Menstrual Disorders | diag..Menstrual.disorders |
| Asthma/COPD | diag..Asthma.COPD |
| Antidiarrheals | med..antidiarrheals |
| Antineoplastic Hormones | med..antineoplastic.hormones |
| Last Albumin | last_albumin_val |
| Last Sodium | last_na_val |
| Last Chloride | last_cl_val |
| Last Hemoglobin | last_hb_val |
| Last Monocyte Percentage | last_monop_val |
| Last RBS Distribution Width (CV), Log | last_rdwcv_val_log |
| Last Shock Index, Log | last_shock_val_log |
| Max Temperature | max_tmp_val |
| Max Blood Urea Nitrogen, Log | max_bun_val_log |
| Median Temperature | median_tmp_val |
| Range Alanine Aminotransferase, Log | range_alt_val_log |
| Range International Normalized Ratio (for prothrombin time), Log | range_inr_val_log |
| Range Lymphocyte Percentage | range_lymp_val |
| Length of Stay, Log1p | length_of_stay_log1p |
| Distinct inpatient episodes within the past 365 days, Log1p | past_inp_count_d365_log1p |
| Distinct emergency episodes within the past 365 days, Log1p | past_emerg_count_d365_log1p |
| Distinct diagnoses (by CCS Category) within past 30 days, Log1p | d30_diag_count_log1p |
| Distinct diagnoses (by CCS Category) within past 90 days, Log1p | d90_diag_count_log1p |
| Distinct medications (by Multum generic name) within past 90 days, Log1p | d90_med_count_log1p |
| Charlson Score, Log1p | charlson_score_log1p |
| Cancer Score | cancer.score |
| Epilepsy/Seizure Score | epilepsy.seizure.score |
| Pneumococcal Pneumonia Score | strep.pneumonia.score |
| Instability Index | instability.index |

| FEATURE NAME | COUNT |
|---|---|
| Cancer Score | 10 |
| Distinct diagnoses (by CCS Category) within past 30 days, Log1p | 10 |
| Instability Index | 10 |
| Last RBC Distribution Width (CV), Log | 10 |
| Length of Stay, Log1p | 10 |
| Distinct inpatient episodes within the past 365 days, Log1p | 10 |
| Charlson Score, Log1p | 8 |
| Max Blood Urea Nitrogen, Log | 6 |
| Non-Ionic Iodinated Contrast Media, Current | 3 |
| Chronic Ulcer of Skin | 3 |
| Last Sodium | 3 |
| Antidiarrheals | 3 |
| Pneumococcal Pneumonia Score | 3 |
| Distinct medications (b Multum generic name) withink past 90 days, Log1p | 2 |
| Last Albumin | 2 |
| Last Hemoglobin | 2 |
| Range Alanine Aminotransferase | 2 |
| Other Upper Respiratory Infection, Current | 1 |
| Viral Vaccines, Current | 1 |
| Distinct diagnoses (by CCS Category) within past 90 days, Log1p | 1 |
| Asthma/COPD | 1 |
| Gout and Other Crystal Arthropathies | 1 |
| Menstraul Disorders | 1 |
| Epilepsy/Seizure Score | 1 |
| Last Chloride | 1 |
| Last Monocyte Percentage | 1 |
| Last Shock Index, Log | 1 |
| Max Temperature | 1 |
| Antineoplastic Hormones | 1 |
| Median Temperature | 1 |
| Distinct emergency episodes within the past 365 days, Log1p | 1 |
| Range International Normalized Ratio (for prothrombin time) | 1 |
| Range Lymphocyte Percentage | 1 |

FIG. 6.

| FEATURE | MIN COEFFICIENT | MAX COEFFICIENT | MEDIAN COEFFICIENT | SIGN CHANGE? |
|---|---|---|---|---|
| Intercept | -15.4277 | -0.83765 | -6.27762 | |
| Cancer Score | 0.214563 | 0.444446 | 0.281333 | |
| Distinct diagnoses (by CCS Category) within past 30 days, Log1p | 0.068964 | 0.24373 | 0.159273 | |
| Instability Index | 0.000654 | 0.184996 | 0.109742 | |
| Last RBC Distribution Width (CV), Log | 0.492195 | 1.423425 | 1.123256 | |
| Length of Stay, Log1p | 0.003413 | 0.308709 | 0.244835 | |
| Distinct inpatient episodes within the past 365 days, Log1p | 0.267715 | 0.541738 | 0.399242 | |
| Charlson Score, Log1p | -0.0276 | 0.282147 | 0.144282 | Yes |
| Max Blood Urea Nitrogen, log | 0.032514 | 0.230887 | 0.118146 | |
| Non-Ionic Iodinated Contrast Media, Current | -0.06718 | 0.503352 | 0.148483 | Yes |
| Chronic Ulcer of Skin | 0.001927 | 0.222477 | 0.050268 | |
| Last Sodium | -0.02351 | 0.003398 | -0.0125 | Yes |
| Antidiarrheals | -0.16499 | 0.050703 | 0.03392 | Yes |
| Pneumococcal Pneumonia Score | -0.13836 | 0.0314 | -0.09173 | Yes |
| Distinct medications (by Multrum generic name) within past 90 days, Log1p | -0.03534 | 0.003402 | -0.01597 | Yes |
| Last Albumin | -0.18337 | 0.107802 | -0.03778 | Yes |
| Last hemoglobin | -0.05015 | 0.01855 | -0.0158 | Yes |
| Range Alanine Aminotransferase | -0.07627 | 0.096665 | 0.010195 | Yes |
| other Upper Respiratory Infection, Current | -0.39004 | -0.39004 | -0.39004 | |
| Viral Vaccines, Current | -0.12352 | -0.12352 | -0.12352 | |
| Distinct diagnoses (by CCS Category) within past 90 days, Log1p | 0.088248 | 0.088248 | 0.088248 | |
| Asthma/COPD | -0.21161 | -0.21161 | -0.21161 | |
| Gout and Other Crystal Arthropathies | -0.40152 | -0.40152 | -0.40152 | |
| Menstrual Disorders | -0.04329 | -0.04329 | -0.04329 | |
| Epilepsy/Seizure Score | 0.007384 | 0.007384 | 0.007384 | |
| Last Chloride | -0.01647 | -0.01647 | -0.01647 | |
| Last Monocyte Percentage | -0.00214 | -0.00214 | -0.00214 | |
| Last Shock Index, Log | 0.052769 | 0.052769 | 0.052769 | |
| Max Temperature | 0.006635 | 0.006635 | 0.006635 | |
| Antineopastic Hormones | 0.080564 | 0.080564 | 0.080564 | |
| Median Temperature | 0.084307 | 0.084307 | 0.084307 | |
| Distinct emergency episodes within the past 365 days, Log1p | 0.066928 | 0.066928 | 0.066928 | |
| Range International Normalized Ration (for prothrombin time) | -0.02898 | -0.02898 | -0.02898 | |
| Range Lymphocyte Percentage | 0.000786 | 0.000786 | 0.000786 | |

*FIG. 7.*

PNEUMONIA READMISSION PREVENTION

BACKGROUND

Pneumonia is an inflammation of the lungs that has a wide range of causes and that can have significant consequences on a patient's health and the healthcare industry. For example, a study of a population of patients found an incidence of community-acquired pneumonia (i.e., pneumonia contracted outside a healthcare facility) to be 18.3 per 1000 people, with a mean hospital admission of 7.6 days and cost of 6,929, and 0.6% of admissions due to community-acquired pneumonia were found to result in patient death. Due to the impact of pneumonia, it is important to accurately and promptly diagnose pneumonia. Additionally, some pneumonia patients are at an increased risk of recurrences, and thus, it is important to take steps to reduce this risk. Some tools exist for determining the severity of pneumonia to determine whether a person should be admitted as a patient, but these tools use a simple rubric that does not take into account patient history or a more holistic view of the patient's condition such that they cannot predict readmission due to pneumonia. Further, existing solutions for predicting readmission utilize patient information that is not available until the time of discharge or even later, limiting the ability to effectuate an actual reduction in the readmission risk through discharge planning.

SUMMARY

Systems, methods and computer-readable media are provided for predicting the probability of a patient's readmission with pneumonia based on information available prior to discharge, utilizing the prediction to provide decision support during discharge of the patient to reduce the risk of readmission. The information used to make the prediction that is available prior to discharge may include labs, vitals, diagnoses, and medications from prior encounters and from the current encounter. In exemplary embodiments, information that is available only at the time of discharge or after discharge is not used. At least some of this information may be used to compute one or more severity metrics for the patient to be input, with other patient information, into one or more prediction models. The severity metrics may include a cancer score, an epilepsy or seizure score, a pneumococcal pneumonia score, and an instability score. An ensemble of machine learning models is applied to the patient information, with each model in the ensemble using a different set of features within the patient information. Each model produces a prediction, and the predictions of all models within the ensemble are combined to generate a prediction of that patient being readmitted with pneumonia within a future time interval. Based on the prediction, one or more intervening actions may be initiated to reduce the probability of readmission. An intervening action may include modifying discharge protocol for the patient based on the predicted probability, including ordering additional testing, ordering medications, providing resources to reduce pneumonia risk for the patient after discharge, adjusting discharge instructions, and scheduling additional examinations or a follow-up appointment with a care provider.

In yet another embodiment, one or more machine learning models are trained to generate the prediction that a patient to be discharged will be readmitted with pneumonia within a future interval. Accordingly, reference information for a reference population may be received, and a plurality of features for predicting readmission may be selected using the reference information. The features may be selected by applying a sequential modeling technique to a potential feature pool. In exemplary aspects, the sequential modeling technique includes an adaptive GLMnet made up of three models being applied successively to the potential feature pool. The potential feature pool may be created by dividing the reference information into categorical features and continuous features. Further, a first gradient tree model may be trained using categorical features, and a second gradient tree model may be trained using continuous features. Potential categorical features are identified using the first gradient tree model, and potential continuous features are identified using second gradient tree model. In exemplary aspects, the potential categorical features, the potential continuous features, and one or more of the severity metrics are combined to create the potential feature pool.

BRIEF DESCRIPTION OF THE DRAWINGS

The present invention is described in detail below with reference to the attached drawing figures, wherein:

FIG. 3 depicts a table mapping medication and diagnoses features input into the ensemble of models, in accordance with an embodiment of the present disclosure;

FIG. 6 depicts a table indicating a count of features in an embodiment of the disclosure actually reduced to practice;

FIG. 7 depicts a table of model coefficients in an embodiment of the disclosure actually reduced to practice.

DETAILED DESCRIPTION

Figure 1A:
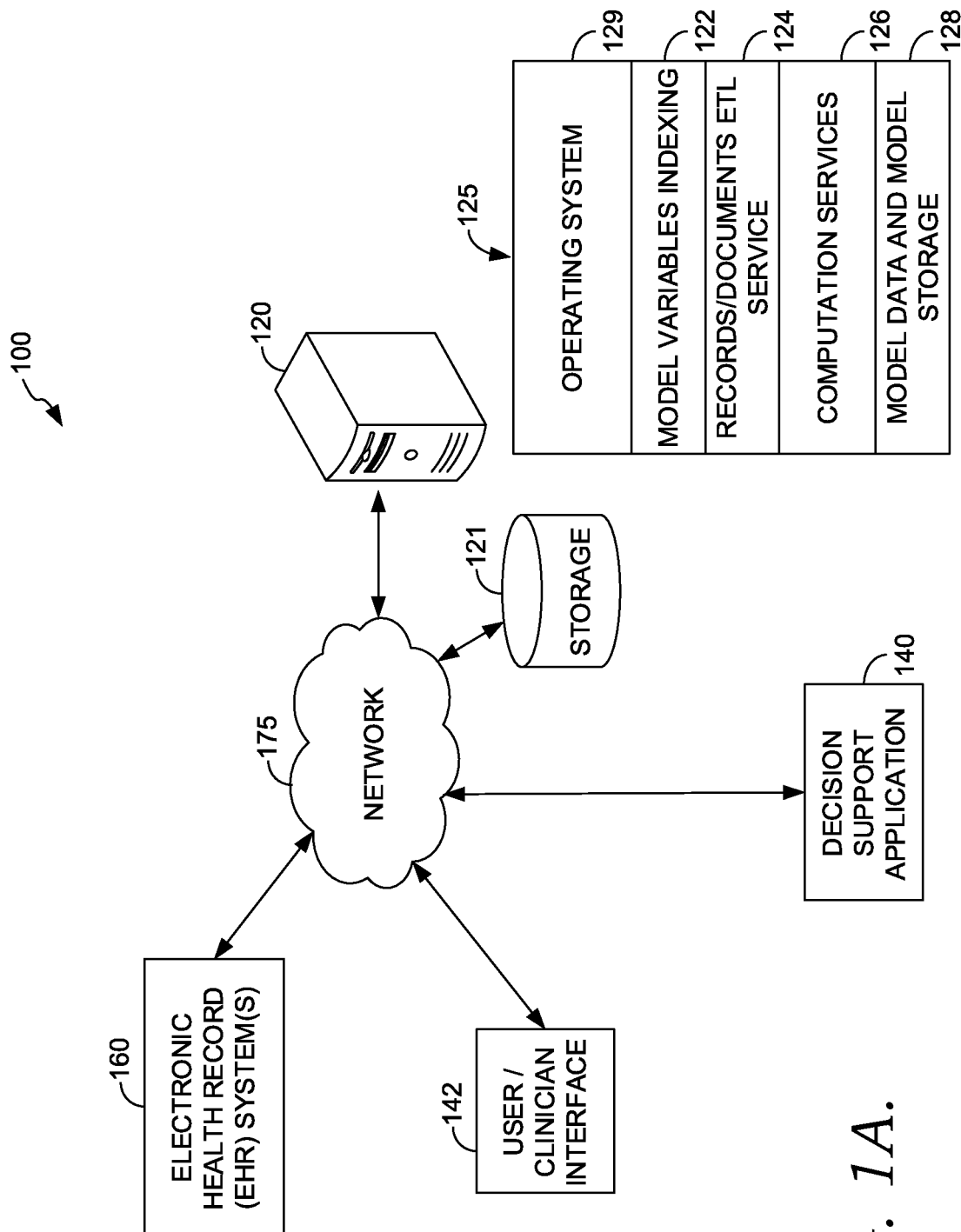
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media, as discussed further with respect to FIGS. 1A-1B.

Accordingly, at a high level, this disclosure describes, among other things, methods and systems for providing decision support during discharge using a prediction of a probability that a patient will be readmitted with pneumonia within a future time interval. In exemplary embodiments, the prediction is generated using one or more machine learning models with information received prior to discharge, such as laboratory results, medication or procedure orders, and diagnoses. This information may include information from previous encounters or the current encounter. At least some of the information available prior to discharge may be used to compute one or more severity metrics for the patient. The severity metrics may include a cancer score, an epilepsy or seizure score, a pneumococcal pneumonia score, and an instability score and may be input into at least some of the one or more machine learning models to determine the probability of readmission. In some embodiments, the methods and systems may be implemented as a decision support computer application or tool for discharge planning for a patient who is diagnosed with and/or treated for pneumonia within the current encounter. For instance, the predicted probability of readmission may trigger one or more intervening actions to reduce the likelihood of readmission, including modifying discharge instructions for the patient, scheduling additional examinations or a follow-up visit, ordering laboratory tests, or ordering one or more medications for the patient.

As previously explained, pneumonia is an inflammation of the lungs, caused primarily, but not exclusively, by infections. Typically, this inflammation causes the alveoli in the lungs to fill with liquid, which can lead to coughing, chest pain, fever, and difficulty breathing. Because of its wide range of causes, pneumonia is typically categorized based on where it was contracted. For instance, hospital (or healthcare)-associated pneumonia (HCAP) is contracted while the patient is in a medical facility, while community-acquired pneumonia (CAP) is contracted in the community, outside of a healthcare setting. The significance of this distinction is that HCAP is more likely to be caused by an antibiotic-resistant pathogen such as methicillin-resistant Staphylococcus aureus, while CAP has a more diverse (and antibiotic-susceptible) range of possible causes (and may not ever have its actual cause recorded at all).

Pneumonia generally and CAP in particular can have significant consequences on a patient's health, which is illustrated through the healthcare costs due to increased patient stays. For example, the mean annual healthcare cost for patients without CAP is 3,783 while the cost to individuals with CAP is 20,961. A study of a population of patients found an incidence of CAP to be 18.3 per 1000 people, with a mean hospital admission of 7.6 days and a cost of 6,929. Not only is CAP costly to the patient and provider, 10.6% of CAP admissions led to death. Due to the impact of pneumonia, the Centers for Medicare and Medicaid Services include pneumonia within their Readmissions Reduction Program, which directly penalizes hospitals with excess readmissions due to pneumonia.

To combat the problems with pneumonia, it is important to accurately and promptly diagnose pneumonia. Some tools exist to assist in determining the severity of pneumonia to determine whether a person should be admitted. For instance, the CURB-65 rubric is a fairly simple rubric in which severity is determined by a count of risk factors; patients get one point for each of the following risk factors (leading to a score between 0 and 5): Confusion, Blood Urea Nitrogen value greater than 7 mmol/L (19 mg/dL), respiratory rate of ≥30 breaths per minute, low blood pressure (systolic blood pressure <90 mmHg or diastolic blood pressure ≤60 mmHg), and age is over 65. Another exiting tool is the Pneumonia Severity Index (PSI), which incorporates a wider range of diagnoses and lab/vital results, as well as assigning different weights to some factors. Yet, PSI is still a checklist where each value gives a fixed number of points, combined to create a final score. The simplistic approach with these existing tools fails to take into account patient history or a more holistic view on patient conditions, which limits the accuracy. Additionally, these existing tools are not ideal for identifying patients who are likely to be readmitted as that information is either not reliably available in the patient's electronic medical records, such as respiratory rate and pleural effusion on an X-ray.

Accordingly, embodiments of the present disclosure aim to accurately identify patients with pneumonia who are likely to readmit for pneumonia during a future time interval. This process may include predicting a likelihood of being readmitted with pneumonia within a future time using information, such as labs, vitals, diagnoses, and medications available prior to discharge. This information may include information from prior encounters and from the current encounter. As such, timely and appropriate intervention can be initiated before the patient is discharged, thereby reducing the likelihood of readmission. Specifically, embodiments include receiving patient information for a patient diagnosed with pneumonia in the current encounter. This information received and used includes information that is available prior to patient discharge. In exemplary embodiments, information that is available after discharge is not used. An ensemble of machine learning models is applied to the patient information, with each model within the ensemble using a different set of features within the patient information. Each model produces a prediction, and the predictions of all models within the ensemble are combined to generate a prediction of that patient being readmitted with pneumonia within a future time interval. Based on the prediction, one or more intervening actions may be initiated to reduce the probability of readmission. An intervening action may include transmitting an electronic notification of the patient's predicted readmission to a remote user device, such as a device associated with the healthcare provider or a device associated with the patient. The intervening action may also include ordering additional testing, ordering medications, providing resources to reduce pneumonia risk for the patient after discharge including modifying discharge instructions, and scheduling intervention with a care provider such as an examination prior to discharge and/or a follow-up visit.

In yet another embodiment, one or more machine learning models are trained to generate the prediction that a patient to be discharged will be readmitted with pneumonia within a future interval. Accordingly, reference information for a reference population may be received, and a plurality of features for predicting readmission may be selected using the reference information. The features may be selected by applying a sequential modeling technique to a potential feature pool. In exemplary aspects, the sequential modeling technique includes an adaptive GLMnet made up of three models being applied successively to the potential feature pool. The potential feature pool may be created by dividing the reference information into categorical features and continuous features. Further, a first gradient tree model may be trained using categorical features, and a second gradient tree model may be trained using continuous features. Potential categorical features are identified using the first gradient tree model, and potential continuous features are identified using second gradient tree model. In exemplary aspects, the potential categorical features, the potential continuous features, and one or more of the severity metrics are combined to create the potential feature pool.

Further, a plurality of prediction models may be trained to predict a likelihood that a patient will be readmitted with pneumonia within a future time interval based on the selected features. Each prediction model may be trained on a different set of features. The plurality of prediction models may comprise an ensemble of models, such as generalized linear models, each providing a probability, and the probabilities may be combined to predict the likelihood of readmission.

Referring now to the drawings generally and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for predicting pneumonia readmission. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or more EHR systems, such as hospital EHR systems, health information exchange EHR systems, ambulatory clinic EHR systems, psychiatry/neurology EHR systems. Such EHR systems may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160 that may be used for storing patient information, it is contemplated that an embodiment may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a graphical user interface operated by a software application or set of applications (e.g., decision support application 140) on a computing device. In an embodiment, the application includes the PowerChart® software manufactured by Cerner Corporation. In an embodiment, the application is a Web-based application or applet. A healthcare provider application may facilitate accessing and receiving information from a user or healthcare provider about a specific patient or set of patients for which the likelihood of being readmitted for pneumonia is predicted according to the embodiments presented herein. Embodiments of user/clinician interface 142 also facilitate accessing and receiving information from a user or healthcare provider about a specific patient or population of patients including patient history; healthcare resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders, such as orders for more resources, from a user based on the results of predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems or other computing device(s) such as computing system 120 described below. In an embodiment, decision support application 140 includes a Web-based application or applet (or set of applications) usable to provide or manage user services provided by an embodiment of the invention. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the invention as described herein. In an embodiment, decision support application 140 sends a recommendation or notification (such as an alarm or other indication) directly to user/clinician interface 142 through network 175. In an embodiment, application 140 sends a maintenance indication to user/clinician interface 142. In some embodiments, application 140 includes or is incorporated into a computerized decision support tool, as described herein. Further, some embodiments of application 140 utilize user/clinician interface 142. For instance, in one embodiment of application 140, an interface component, such as user/clinician interface 142, may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some embodiments, application 140 and/or interface 142 facilitates accessing and receiving information from a user or health care provider about a specific patient, a set of patients, or a population according to the embodiments presented herein. Such information may include historical data; health care resource data; variables measurements, time series, and predictions (including plotting or displaying the determined outcome and/or issuing an alert) described herein; or other health-related information. Application 140 and/or interface 142 also facilitates the display of results, recommendations, or orders, for example. In an embodiment, application 140 also facilitates receiving orders, scheduling time with care providers (including follow up visits), or queries from a user, based on the results of the forecasted pneumonia readmission risk, which may utilize user interface 142 in some embodiments.

Decision support application 140 may also be used for providing diagnostic services or evaluation of the performance of various embodiments. As shown in example environment 100, in one embodiment, decision support application 140, or the computer system on which it operates, is communicatively coupled to monitor 141 via network 175. In an embodiment, patient monitor 141 communicates directly (or via network 175) to computer system 120 and/or user/clinician interface 142. In an embodiment, monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables. It is also contemplated that the clinical or physiological information about a patient or population of patients, such as the monitored variables, patient demographics, patient history, and/or clinical narratives regarding the patient, used according to the embodiment of the invention disclosed herein may be received from a patient's historical data in EHR system 160, or from human measurements, human observations, or automatically determined by sensors in proximity to the patient.

An embodiment of monitor 141 stores user-derived data locally or communicates data over network 175 to be stored remotely. In an embodiment, decision support application 140, or the computer system it is operating on, is wirelessly communicatively coupled to monitor 141. Application 140 may also be embodied as a software application or app operating on a user's mobile device, as described above. In an embodiment, application 140 and monitor 141 are functional components of the same device, such as a device comprising a sensor, application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or the computer system supporting application 140 for performing signal conditioning of a measured patient variable. In one embodiment, computer system 120 comprises one or more computing devices, such as a server, desktop computer, laptop, or tablet, cloud-computing device or distributed computing architecture, a portable computing device such as a laptop, tablet, ultra-mobile PC, or a mobile phone.

Embodiments of computer system 120 include computer software stack 125, which, in some embodiments, operates in the cloud as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 142 and/or decision support application 140. In some embodiments, user/clinician interface 142 and/or decision support application 140 operate in conjunction with software stack 125.

In embodiments, model variables indexing service 122 provide services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing one or more models for predicting pneumonia readmission as described in connection to methods 200, 400, and 500 of FIGS. 2, 4, and 5, respectively.

Computation services 126 perform statistical software operations, such as computing the transformed variable predictions, transferred features (such as log and log 1p functions of features), and severity indices as described herein. In an embodiment, computation services 126 and predictive models service 124 include computer software services or computer program routines. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for utilizing performing sequential modeling using one or more models, including decision trees and logistic models, for predicting pneumonia readmission, such as the models described in connection to FIGS. 2-8C.

In some embodiments, stack 125 includes file system or cloud-services 128. Some embodiments of file system/cloud-services 128 may comprise an Apache Hadoop and Hbase framework or similar frameworks operable for providing a distributed file system and which, in some embodiments, provide access to cloud-based services such as those provided by Cerner Healthe Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
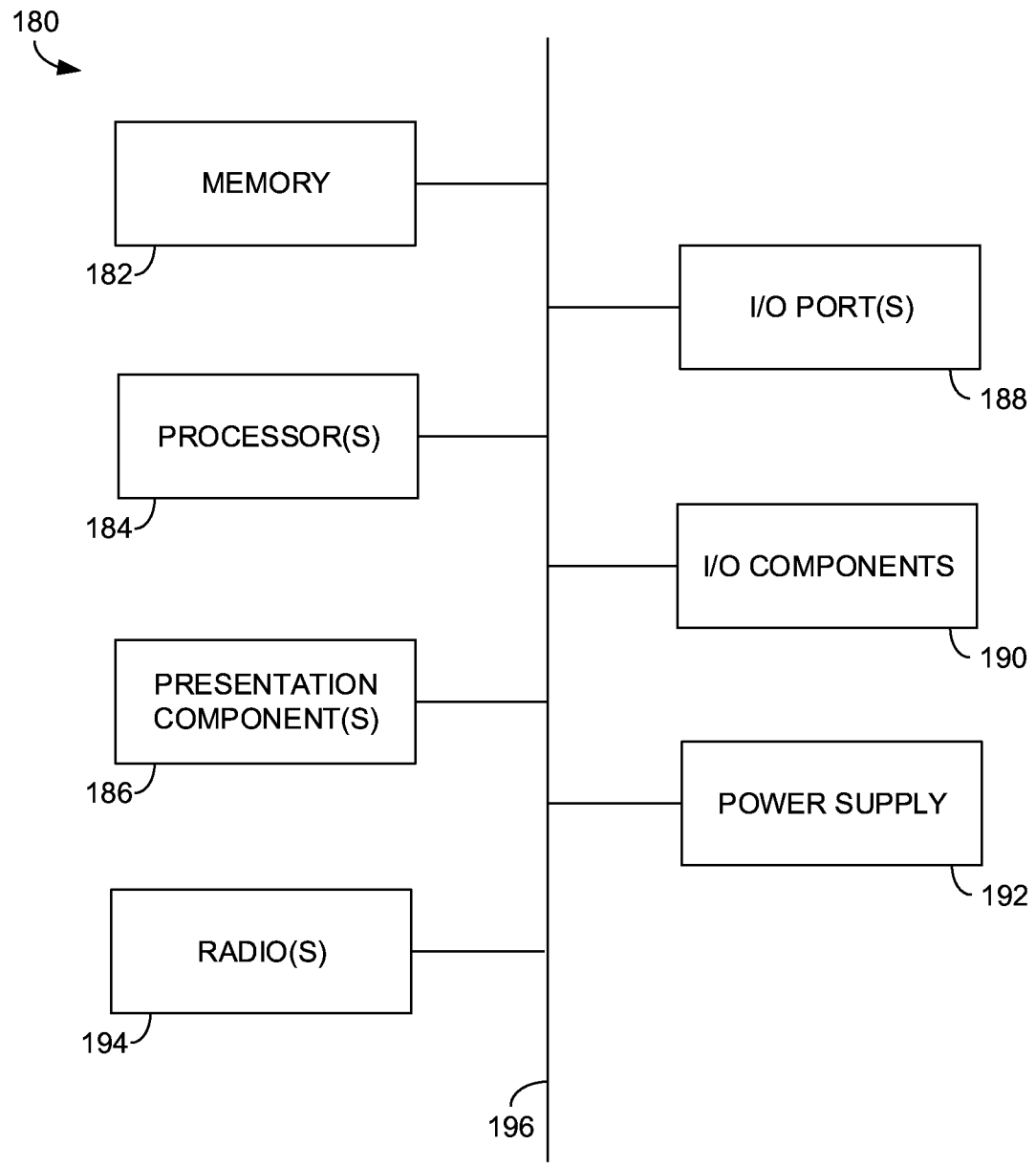

Turning briefly to FIG. 1B, there is shown one example embodiment of computing system 180 representative of a system architecture that is suitable for computer systems such as computer system 120. Computing system 180 includes a bus 182 that directly or indirectly couples the following devices: memory 184, one or more processors 186, one or more presentation components 188, input/output (I/O) ports 190, input/output components 192, radio 196, and an illustrative power supply 194. Bus 182 represents what may be one or more busses (such as an address bus, data bus, or combination thereof). Although the various blocks of FIG. 1A are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1A is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 184 includes computer storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 184 or I/O components 192. Presentation component(s) 188 present data indications to a user or other device. Exemplary presentation components include a display device, speaker, printing component, vibrating component, etc.

In some embodiments, computing system 180 comprises radio(s) 196 that facilitates communication with a wireless-telecommunications network. Illustrative wireless telecommunications technologies include CDMA, GPRS, TDMA, GSM, and the like. Radio 196 may additionally or alternatively facilitate other types of wireless communications including Wi-Fi, WiMAX, LTE, or other VoIP communications. As can be appreciated, in various embodiments, radio 196 can be configured to support multiple technologies and/or multiple radios can be utilized to support multiple technologies.

I/O ports 190 allow computing system 180 to be logically coupled to other devices, including I/O components 192, some of which may be built in. Illustrative components include a microphone, joystick, game pad, satellite dish, scanner, printer, wireless device, etc. The I/O components 192 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Decision-Support for Reducing Risk of Pneumonia Readmission

Figure 2:
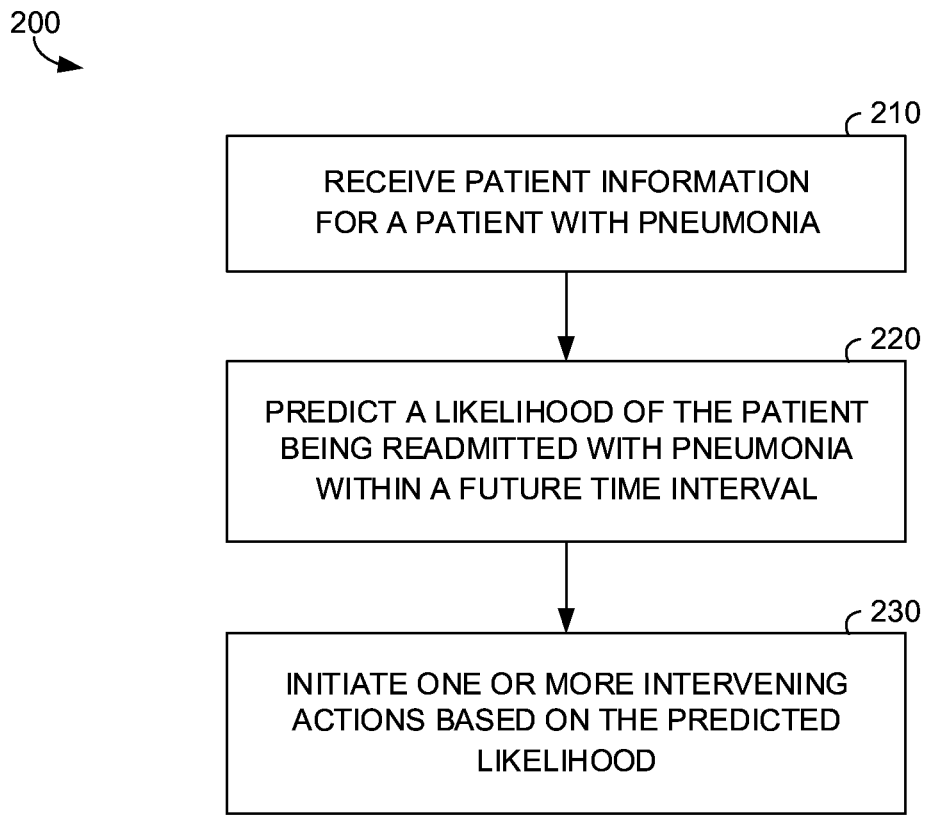
FIG. 2 depicts a flow diagram of a method for reducing pneumonia readmissions, in accordance with an embodiment of the disclosure.

Turning now to FIG. 2, an example embodiment of a method for reducing the risk of or preventing pneumonia readmission is provided and is referred to generally as method 200. In particular, example method 200 utilizes an ensemble of machine learning models with patient information available prior to discharge to predict a likelihood that the patient will be readmitted with pneumonia within a future time interval and providing an intervention corresponding to the predicted likelihood. In some embodiments, method 200 is suitable for implementation as a computer-performed decision support tool or application for providing care to pneumonia patients or discharge planning for pneumonia patients based on a predicted readmission likelihood that is more accurate than conventional technology would otherwise allow.

In accordance with method 200, at step 210, a plurality of patient information is received. The patient information may comprise current patient data, patient demographic data, and/or historical patient data. In exemplary aspects, current patient data includes data relating to the patient's current encounter (e.g., the current admission into the healthcare facility). The current encounter information may include a diagnosis of and/or treatment for pneumonia, which may be community-acquired, healthcare-associated, viral, bacterial, and the like. During the current encounter, the patient may be diagnosed with or treated for other conditions, such as asthma, chronic obstructive pulmonary disease, chronic ulcer of skin, lung cancer, neoplasms, gastrointestinal cancer, epilepsy, for example. Current patient information may further include medication orders and lab results from the current encounter.

Patient demographics may include age, sex, race, nationality, socioeconomic status, marital status, and/or employment status. This data may further include the patient's insurance information, such as the insurance provider and the type of plan. Further, historical patient data may include the patient's medical history and/or family history. Historical patient data may also include information about the patient's past encounters at the current healthcare facility or other facilities. In exemplary embodiments, historical patient data includes previous diagnoses, medications, and lab results. In some embodiments, the information received is limited to a predetermined past time frame, such as the past two years.

This patient information may be received from different sources. For instance, in one embodiment, all patient data is received at step 210 from the patient's EMR. In other embodiments, data relating to the patient's current condition and/or patient demographics may be received directly from a user, such as the patient or a care provider, inputting such information into a user device. Some current patient data, such as patient variable values, may be received from one or more sensors or monitoring devices or directly from a laboratory running the laboratory procedures. Additionally, historical patient information may be received from the patient's EMR and/or from insurance claims data for the patient. In an alternative embodiment, the patient's history may be received directly from the patient, such as during registration when admitted for the current encounter.

At step 220, the patient's likelihood of being readmitted with pneumonia within a future time interval is predicted using a plurality of machine learning models on least some of the patient information that is available and received prior to patient discharge. In exemplary embodiments, the future time interval is 30 days from the current encounter such that it is predicted whether the patient will be readmitted with pneumonia within 30 days of discharge in the current encounter. The patient information may include lab results, vital sign measurements, diagnoses, and medication history from the current encounter as well as prior encounters. In exemplary aspects, the patient information used to predict pneumonia readmission is information is only information that is available prior to discharge. In other words, information that becomes available at the time of discharge of the current encounter or after is not used.

The prediction for readmission is generated using an ensemble of models operating on different sets of variables (referred to herein as features). In some embodiments, the ensemble of models (or ensemble modeling) is used to determine a composite prediction from a set of multiple, diverse models each created to predict an outcome or contribute towards predicting an outcome. In some embodiments, each model in the ensemble (which may also be referred to as a member of the ensemble) comprises a different modeling algorithm and/or may be generated using different training data sets. In exemplary aspects, for instance, the predictor is an ensemble of ten machine learning models, such as generalized linear models, where each member model is created with (and thus applied to) to a different set of features within the patient's data to output a predicted probability of the patient being readmitted with pneumonia. The prediction (or contribution) of each member model may be aggregated or combined to generate a composite prediction (also referred to herein as an overall prediction) for the unseen data. For example, the overall prediction may be the mean of the probabilities computed by all of the member models. In some embodiments, the individual prediction of each ensemble member is weighted equally when determining the overall, composite prediction. In another embodiment, the ensemble member model predictions may be assigned different weights. In some embodiments, the weighting may be based on learned feedback about prior predictions The combinations of features used with the ensemble of models may include features relating to diagnoses, medications, hospitalization history, laboratory results, and severity metrics, for example. These features are discussed in greater detail below. The ensemble may use different combinations of these types of features. In one embodiment, for example, 33 different features were used with 10 models.

Features relating to diagnosis and/or medications may include features based directly on diagnoses or medications. Relevant diagnoses may include other upper respiratory infection, asthma, gout, chronic obstructive pulmonary disease, and relevant medications may include albuterol, non-ionic iodinated contrast media, or viral vaccines associated with one or more of these diagnoses. The presence of a diagnosis or medication may be relevant in the current encounter only or in the patient's history, which may include the current encounter. Current medications, for example, include medications recorded as being prescribed during the patient's current encounter, while historical medications include medications recorded at any encounter within a past time frame, such as two years.

In exemplary aspects, identification of these diagnoses/medication features are based on the patient EHR. For instance, for diagnoses, an ontology mapping scheme may be used to map diagnostic codes to common nomenclature. For medications, an ontology mapping scheme may be used to map a medication in the EHR to a "drug classification" concept to collect the generic name of the medication. In exemplary embodiments, features directly relating to diagnoses or medications are binary such that the feature is either present or absent from the patient record. FIG. 3 depicts a reference table 300 that is used in some embodiments to map human and code names for various features input into the ensemble of models.

In one embodiment, the following diagnoses/medication features are used within the ensemble:
  Other Upper Respiratory Infection (diagnosis), Current Encounter;
  Non-Ionic Iodinated Contrast Media (medication), Current Encounter;
  Viral Vaccines (medication), Current Encounter;
  Chronic Ulcer of Skin (diagnosis), Past 2 Years including Current Encounter;
  Gout and Other Crystal Arthropathies (diagnosis), Past 2 Years including Current Encounter;
  Menstrual Disorders (diagnosis), Past 2 Years including Current Encounter;
  Asthma/COPD, Past 2 Years including Current Encounter, which may be identified by:
    Diagnosis in the CCS Category "Asthma";
    Diagnosis in the CCS Category "Chronic obstructive pulmonary disease and bronchiectasis";
    Medication with generic name "albuterol";
    Medication with generic name "albuterol-ipratropium";
    Medication with drug classification "anticholinergic bronchodilators";
    Medication with generic name "formoterol";
  Antidiarrheals (medication), Past Two Years including Current Encounter; and
  Antineoplastic Hormones (medication), Past Two Years including Current Encounter.

Note that at least some of the features listed above and discussed below (including the severity metrics) include a reference to the past two years. Reference to the past two years means that information may come from previous encounters within a predetermined past time frame. In some exemplary embodiments, this past time frame is two years. However, it is contemplated that other time frames, such as one year, three years, five years, and the like may be used instead. As such, reference to the "past two years" with respect to the features is a reference to a predetermined past time frame that may be longer or shorter than the past two years.

Laboratory features with laboratory and clinical event values may also be used to predict pneumonia readmission. Laboratory features may include measurements performed within the current encounter and/or over a previous time frame, such as the past two years. In some embodiments, labs performed within the last two hours of the current encounter are excluded. The laboratory features may be in the form of a "last" value, a "max" value, a "min" value, a "median" value, and a "range".

As used herein, the "last" value may refer to the most recent available value for that laboratory procedure. The "max" value may refer to the highest value found in a past time frame, such as one year. In some aspects, if there are no values in the past time frame but are values from before that, then the most recent value may be used as the "max" value. The "min" value may refer to the lowest value in a past time frame, such as one year, or, in some aspects, the most recent value if there are no values in the relevant past time frame. The "median" value may refer to the middle-most value (or the mean of the two middle-most values, if the count is even) of all values within the past time frame, such as one year. In some aspects, if no values are in the relevant past time frame, the most recent value may be used for the median. Lastly, the "range" value may refer to the difference between the max and min value computed as previously described. In some embodiments, a value for a lab feature may be imputed if the value is missing entirely. Further, some lab features may comprise transformed lab values, such as values transformed using log and log 1p functions. In some embodiments, log and log 1p, as used herein, refer to the natural logarithm functions. Further, in exemplary aspects, the log 1p function refers to a function that performs a log transform on the sum of a given feature value plus one, which enables use of the function of features that may have a zero value.

In one embodiment, the following laboratory features are used within the ensemble:
  Last Values
    Albumin (Imputed value: 3.3 g/dL)
    Sodium (Imputed value: 138 mmol/L)
    Chloride (Imputed value: 102 mmol/L)
    Hemoglobin (Imputed value without anemia: 12; Imputed value with anemia: 10.2 g/dL)
    Monocyte Percentage (Imputed value: 8%)

Log of RBC Distribution Width (CV) (Imputed value without anemia: ln(14.1%); Imputed value with anemia: ln(15.1%))

Log of Shock Index (in terms of ratio of heart rate to systolic blood pressure) (Imputed value: ln(82 bpm/127 mmHg))

Max Values

Temperature (Imputed value: 100° F.)

Log of Blood Urea Nitrogen (BUN) (Imputed value without AM or CKD: ln(21 mg/dL); Imputed value with AM or CKD: ln(40 mg/dL))

Median Values

Temperature (Imputed value: 98.1° F.)

Range Values

Alanine Aminotransferase (Imputed value without liver disease: 7 units/L; Imputed value with liver disease: 22 units/L)

International Normalized Ratio (for prothrombin time) (Imputed without a history of warfarin, embolisms, dysrhythmias, or heart valve disorders: 0; Imputed with a history of warfarin, embolisms, dysrhythmias, or heart valve disorders: 0.12)

Lymphocyte Percentage (Imputed without a history of anemia: 10%; Imputed with a history of anemia: 16%)

Some of these values may be found directly in the patient's records while other values may be calculated. For example, if the patient's record does not include a monocyte percentage but does have monocyte count and total white blood count, the monocyte percentage may be calculated from those other values.

Features may also be based on the patient's hospitalization history, such as the patient's length of stay, number of past inpatient and emergency encounters, and number of distinct diagnoses. In exemplary embodiments, values associated with the patient's hospitalization history are transformed using log 1p function when used as features within the ensemble. In one embodiment, the following hospitalization history features are used within the ensemble:

Length of Stay

Log 1p of length of stay, measured in hours

Past Encounter Counts

Log 1p of count of distinct inpatient episodes within the past 365 days

Log 1p of count of distinct emergency episodes within the past 365 days

Past Diagnosis/Medication Counts

Log 1p of count of distinct diagnoses (as determined by a database hierarchy, such as CCS) within past 30 days Log 1p of count of distinct diagnoses (e.g., by CCS Category) within past 90 days Log 1p of count of distinct medications (e.g., by generic name) within past 90 days Further, one or more severity metrics may be computed and used to predict the patient's likelihood of a pneumonia readmission. These severity metrics may relate to comorbidities, specific conditions, lab results, and/or vital sign values. Unlike with the diagnosis/medication features, these features are not binary, and unlike the laboratory features, there is a limited set of possible values. Instead, these metrics are designed to incorporate certain warning signs indicating a patient has or will have a deteriorating condition into a feature that can be easily processed through a prediction model. In other words, these metrics summarize different signs and metrics into a single feature that a model can process more easily without losing the distinction that more signs are worse than fewer. In exemplary aspects, severity metrics include one or more of a cancer score and an instability score. In other embodiments, an epilepsy/seizure score and/or a pneumococcal pneumonia score may be used. The prediction may further be based on one or more of a peptic ulcer score, a hypertension score, a mood/psychosis score, a blood thinner score, an asthma/COPD score, and a neuropathy score.

These severity scores represent unconventional metrics for measuring patient health and predicting pneumonia. Further, these unconventional scores help to provide an accurate prediction using the ensemble of models without the use of information typically received only at or after discharge. In this way, these scores and their use within the prediction models to reduce pneumonia readmission are unconventional and improve upon existing decision support tools. Further aspects of the present disclosure also utilize a Charlson score, a severity metric derived from the Charlson Comorbidity index, with one or more of the other severity scores.

A cancer score may indicate whether a patient has received a cancer diagnosis within a relevant time frame, such as two years. As such, determining a cancer score for a patient may include identifying the presence of one or more cancer diagnoses, assigning each diagnoses with a point level, and combining the assigned points. For instance, each diagnoses may be assigned one point, all points may be added together, and a cap (or maximum score) may be applied to obtain the cancer score for that patient. In exemplary aspects, the cancer score is capped at three such that values above three after summing the points are replaced with a score of three. In some aspects, only diagnoses within a predetermined time frame, such as two years including the current encounter, are included in computing the cancer score. In an example embodiment, the following cancers or related treatments are each assigned a point if identified in the patient's record: cancer of bronchus, lung; secondary malignancies; other gastrointestinal cancer; cancer of lymphatic and hematopoietic tissue; neoplasms of an unspecified nature or uncertain behavior; maintenance chemotherapy; and radiotherapy.

An instability score may be determined based on values of the patient's lab results. These values may indicate a degree of instability or deterioration of the patient. These lab result values may be determined from the most recent value, whether the value is in the current encounter or a past encounter. In alternative embodiments, the value is only used if it is in the current encounter. In one embodiment, one point is assigned to the presence of each lab result value indicated below:

Calcium<8.25 mg/dL

Hematocrit<34%

Albumin<3 g/dL

Bicarbonate≥32 mmol/L

Chloride<100 mmol/L

Serum Creatinine≥1.3 mg/dL

Lymphocyte Percentage<10%

Further, in exemplary embodiments, the instability score is capped at a maximum value of 5. In some embodiments, where a value for a lab result is not found, 0 points is given, but 1 point may be imputed for the hematocrit value when the patient has anemia.

A pneumococcal pneumonia score may be determined by assigning a point for having each of: (i) a diagnosis of pneumonia due to Streptococcus pneumonia during the current encounter; (ii) a medication prescribed during the current encounter relating to symptoms of pneumococcal pneumonia; and (ii) a medication of a related vaccine prescribed during the current encounter. The diagnosis of pneumonia due to Streptococcus pneumonia may be determined by a diagnosis defined by the ICD-9 or ICD-10 categories. Medications relating to symptoms of pneumococcal pneumonia may include ceftriaxone, cefotaxime, ampicillin-sulbactam, azithromycin, or moxifloxacin. The vaccine may include either pneumococcal 13-valent conjugate vaccine," "pneumococcal 23-valent vaccine (obsolete)," or "pneumococcal 23-polyvalent vaccine". If a patient's records include multiple items within one of the three categories above, only one point may be assigned for that category in accordance with some embodiments of the invention. Additionally, the points may be summed and capped at a maximum pneumococcal pneumonia score of two.

Further, an epilepsy/seizure score may be determined in a similar fashion. The epilepsy/seizure score may, thus, indicate whether the patient has had a diagnoses of epilepsy or other condition associated with seizures and/or whether the patent has been prescribed an associated medication. For instance, one point may be given to select diagnoses and medications relating to seizures and/or epilepsy, the points may be summed, and a cap may be applied. In one embodiment, one point is assigned for the presence of each of the following:

Diagnosis in group "Epilepsy; Convulsions" during the past two years (including current encounter)

Diagnosis in the group "Other connective tissue disease" during the past two years (including current encounter)

Medication of "Skeletal Muscle Relaxants" (grouped by drug classification) in medication history table during the past two years (including current encounter)

Medication of "phenobarbital" (grouped by generic name) or "Miscellaneous Anticonvulsants" (grouped by drug classification) in medication history table during the past two years (including current encounter)

Medication of "Miscellaneous Anticonvulsants" (grouped by drug classification) prescribed during the current encounter Medication of "diazepam" (grouped by generic name) during the past two years (including current encounter)

Where there is multiple items within one of the above diagnosis or medication groups, only one point is given. In exemplary embodiments, the score is capped at 3.

As previously stated, one severity metric that may be used is referred to as the Charlson score derived from the conventional Charlson Comorbidity index. The Charlson score is obtained by applying weights to particular conditions. For instance, a weight of one may be applied to chronic obstructive pulmonary disease, renal conditions like chronic kidney disease or chronic nephrotic syndrome), rheumatoid arthritis, and diabetes with complications. A weight of two may be applied to malignant neoplasms, mild liver disease, congestive heart failure, dementia, and paraplegia/paralytic syndromes. A weight of two may be applied to severe liver disease and HIV/AIDS, while a weight of six may be applied to metastatic neoplasms. Each condition may be identified via a coding algorithm, such as ICD-9 and ICD-10, assigned a weight, and then added into a patient's Charlson score. The final value for the Charlson score may be transformed using the log 1p function.

In embodiments utilizing a peptic ulcer score, the peptic ulcer score may be computed by assigning a point for the presence of each of the following: (i) a diagnosis in the category "Gastroduodenal ulcer (except hemorrhage)" during the current encounter; (ii) medication of "H2 antagonists" (grouped by drug classification) prescribed or in medication history during the past two years (including current encounter); and (iii) medication of "proton pump inhibitors" (grouped by drug classification) prescribed or in medication history during the past two years (including current encounter). In some embodiments, if there are multiple items within one of the above categories in the patient's electronic record, a maximum of one point is assigned for each category. The total points may be summed, and a cap of two may be applied.

Similarly, a hypertension sore may be determined by adding the points assigned for the presence of each of the following:

diagnosis in the group "Hypertension" during the past two years (including current encounter);

any of the following medications (grouped by drug classification) during the past two years (including current encounter), with each medication counting separately (e.g., multiple points are given for multiple medications):

angiotensin converting enzyme (ACE) inhibitors
calcium channel blocking agents
loop diuretics
beta blockers, cardioselective
beta blockers, non-cardioselective
vasodilators
vasopressors In example embodiments, this hypertension score is capped at seven points.

A mood/psychosis score may be determined by assigning one point for each of the following medications (grouped by drug classification) during the past two years (including the current encounter):

miscellaneous anxiolytics, sedatives and hypnotics
miscellaneous antipsychotic agents
phenylpiperazine antidepressants The points may be summed together with a capped score of two points.

An asthma/COPD score may be determined by assigning one point for each of the following diagnosis and medications relating to asthma or chronic obstructive pulmonary disease:

Diagnosis in the groups "Asthma" or "Chronic obstructive pulmonary disease and bronchiectasis" during the past two years (including current encounter)

Medication of "albuterol" or "albuterol-ipratropium" (grouped by generic name) prescribed or in medication history during the past two years (including current encounter)

Medication of "anticholinergic bronchodilators" (grouped by drug classification) prescribed or in medication history during the past two years (including current encounter)

Medication of "glucocorticoids" (grouped by drug classification) prescribed or in medication history during the past two years (including current encounter)

In exemplary aspects, the sum of the points is capped at one point.

A blood thinners score may be determined by assigning one point for each of the following medications (grouped by drug classification) in the patient's medication history during the past two years (including the current encounter):

platelet aggregation inhibitors
coumarins and indanediones
heparins
factor Xa inhibitors The points may be summed together with a capped score of two points.

A neuropathy score may be determined by assigning one point for each of the following diagnoses and medications:

Diagnosis in the group "Other nervous system disorders" during the past two years (including current encounter)

Medication of "gabapentin" or "pregabalin" (grouped by generic name) prescribed or in medication history during the past two years (including current encounter)

Medication of "carBAMazepine" or "OXcarbazepine" (grouped by generic name) prescribed or in medication history during the past two years (including current encounter)

Medication of "SSNRI antidepressants" (grouped by drug classification) prescribed or in medication history during the past the two years (including current encounter)

Medication of "tricyclic antidepressants" (grouped by drug classification) prescribed or in medication history during the past two years (including current encounter)

Medication of "buPROPion" (grouped by generic name) prescribed or in medication history during the past two years (including current encounter)

In exemplary aspects, only one point is given when there are multiple items within a particular bulleted group above. Additionally, the sum of the points for the neuropathy score is capped at three points.

Returning to method 200 of FIG. 2, at step 230, one or more intervening actions may be initiated based on the predicted likelihood of readmission with pneumonia. In some embodiments, an intervening action may include emitting or otherwise electronically communicating a recommendation or notification to a caregiver responsible for the patient's care, such as a physician or nurse. This notification may be presented via a user/clinician interface (such as interface 142 described in FIG. 1A). The notification may indicate the predicted probability of the patient being readmitted with pneumonia within the future time interval and/or present instructions to not discharge the patient or to discharge patient with particular discharge instructions. Additionally, some embodiments of step 230 may further include storing the result of the pneumonia readmission prediction in an EHR associated with the patient and further may include providing the patient's EHR (or facilitating access to the EHR) in the notification.

In example embodiments, an intervening action may include modifying the patient's discharge protocol to one that is designed to reduce the likelihood of readmission. The modified discharge protocol may include requiring additional approval of discharge by a care provider (which may require further examination by a care provider), providing discharge instructions tailored to reduce the risk of readmission due to pneumonia, scheduling a follow up appointment with a care provider within a specified time from discharge, ordering additional testing, and prescribing medications designed to reduce the risk of pneumonia developing. As such, an intervening action may include scheduling a time for a care provider to see the patient prior to discharge or scheduling a follow-up appointment within a designated time period that is less than the time period (e.g., 30 days) for which the pneumonia readmission is forecasted. An intervening action may also include electronically adding one or more documents with special discharge instructions to a queue associated with the patient's record, which may include a queue designating documents for printing and/or providing to the patient. One or more care providers, such as a discharge nurse, may be notified of the additional documentation. Further, additional testing to confirm the increase risk and medications may be ordered prior to patient's discharge.

One or more of these intervening actions may be performed by automatically modifying computer code executed in a healthcare software program for treating the patient and/or discharging planning, thereby transforming the program at runtime. For example in one embodiment, the modification comprises modifying (or generating new) computer instructions to be executed at runtime in the program, the modification may correspond to a change in a discharge procedure due to the predicted readmission.

In some embodiments, the intervening actions may be initiated automatically when the probability of readmission satisfies a threshold level (i.e., a threshold probability). The threshold level may vary depending on the action. For instance, a threshold probability may be set for providing additional discharge instructions such that, when the threshold is satisfied, an action for providing additional discharge instructions is automatically initiated. A different threshold, such as a higher probability, may be set for initiating an exam by a care provider to approve discharge or for ordering additional testing. As used herein, satisfying a threshold may refer to meeting or exceeding a threshold value.

Building a Pneumonia Readmission Predictor

Figure 4:
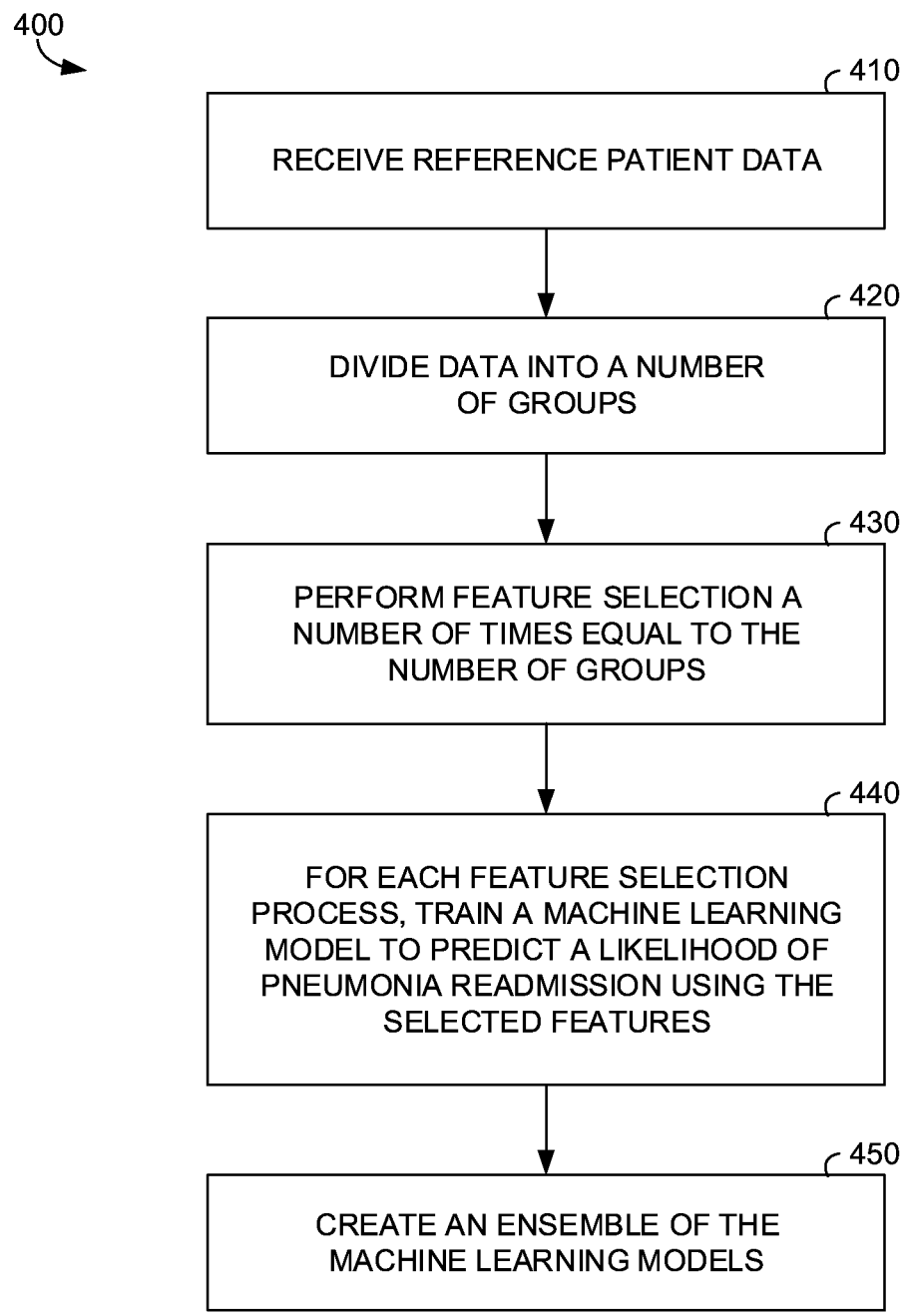
FIG. 4 depicts a flow chart of a method for building a pneumonia readmission predictor suitable for use within a decision support system, in accordance with an embodiment of the disclosure.
Figure 5:
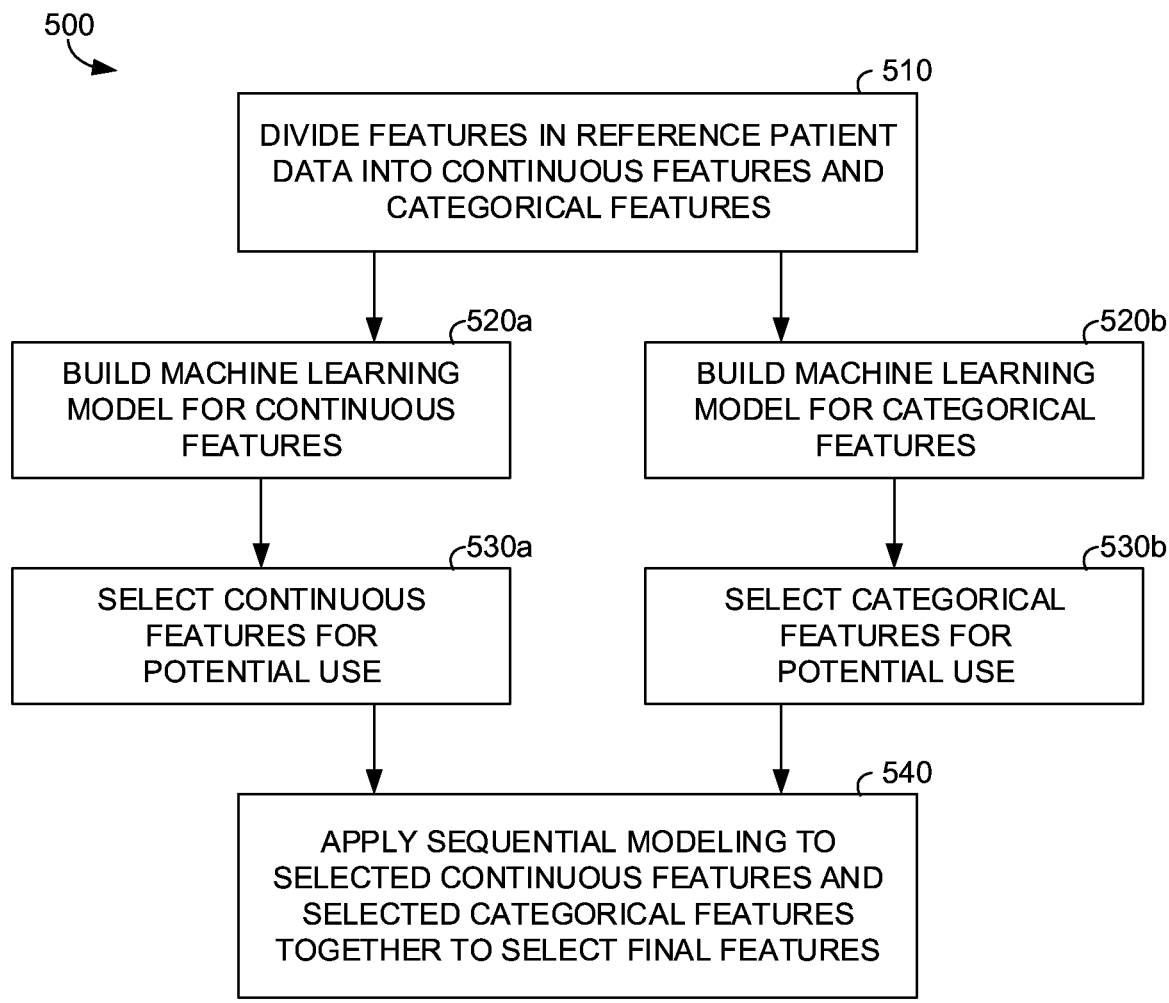
FIG. 5 depicts a flow chart of a method for selecting features for a pneumonia readmission predictor suitable for use within a decision support system, in accordance with an embodiment of the disclosure.

FIGS. 4-5 illustrate example processes for building a pneumonia readmission predictor, including selecting features for use in the predictor, are provided. As described in greater detail below with respect to FIGS. 4 and 5, a variety of machine learning models may be utilized in predicting pneumonia readmissions. For instance, prediction model(s) may be used to predict pneumonia readmission while feature selection models may be used to identify and select the features or feature sets that are used with the prediction model(s). Further, the feature selection models may include potential feature selection models and final feature selection models. Additionally, these models may use different types of machine learning algorithms. For instance, a first type (such as a gradient boosted tree model) may be used to select features for a potential feature pool, a second type (such as an adaptive GLMnet) may be used for selecting final feature sets, and a third type (such as generalized linear models) such as may be used for generating the actual prediction.

Turning to FIG. 4, a flow chart is depicted to illustrate an example method 400 for building a pneumonia readmission predictor for providing decision support through discharge planning of pneumonia patients. At step 410, reference patient data is received. The reference population of patients includes patients discharged from a healthcare facility after being diagnosed with and/or treated for pneumonia. The patient data includes information, such as diagnoses, medications, lab results, vital signs, that was available prior to discharge.

In exemplary aspects, some features may be removed from the reference patient data as a pre-processing step. The removed features may include features not available prior to the time of discharge the patient. In some embodiments, the removed features further included: features tied to specific hospitals, features tied to prior outpatient duration, medications used by a very small fraction of encounters, and binary features that are present only in 1% or fewer of encounters.

At step 420, the reference patient data may be divided into a number of groups, with each group representing a subset of patients with the reference population. In exemplary embodiments, the reference patient data is divided into ten groups. At step 430, feature selection is performed a number of times equal to the number of groups so that a number of feature sets equal to the number of groups is created. As such, in exemplary embodiments, feature selection is performed ten times. Each time feature selection is performed, it is performed on the number of groups minus one. For instance, where there are ten groups, feature selection is performed on nine groups with one group being held out. The group being held out of feature selection changes each time feature selection is performed. The process of feature selection is detailed in FIG. 5.

For each feature set that is selected in step 430, a machine learning model may be trained to predict a likelihood of pneumonia readmission using the selected feature set as indicated at step 440. In exemplary aspects, the machine learning model is a generalized linear model. For instance, the models may be logistic regression models; however, it is contemplated that other generalized linear models may be used.

At step 450, an ensemble of models is created from the plurality of machine learning models built for each feature set in step 430. This ensemble may be used to predict pneumonia readmission risk as described in step 220 with respect to FIG. 2. As such, the models within the ensemble may be run simultaneously on new patient data, and each model may generate a likelihood of a patient being readmitted with pneumonia within future time interval, such as 30 days. The predicted risk, which may be in the form of a probability, from each model may be combined to determine an overall risk level or probability. For instance, the overall risk for a target patient may be the average probability output from the models within the ensemble. Further, the overall risk may be used to trigger intervening action, through a decision-support tool for discharge planning for example, to reduce the risk of readmission.

Turning to FIG. 500, an example method 500 for selecting the features to use in a pneumonia readmission predictor (e.g., an ensemble of a plurality of models) is depicted. In exemplary aspects, features for this pneumonia readmission predictor are chosen in a sequential process, with each step removing some features and leaving others to be processed by following steps (or to remain in a final model). As illustrated through method 500, feature selection may comprise a feature-type-specific selection and a general selection. As such, at step 510, features within the received reference patient data are divided according to the type of feature. In exemplary aspects, as indicated in FIG. 5, the data is divided into continuous features and categorical features. Categorical features have only two or three possible values. Example categorical features includes the presence or absence of a medication or diagnosis. Continuous features are features with more than three possible values and often include lab results and vital signs. The features may be divided this way so that an initial selection model can be run while taking into account potential basis for certain types of features. For instance, it may be desirable for a gradient tree decision algorithm to be applied to these features separately because such an algorithm is biased towards features with higher cardinality.

Accordingly, for each type of feature, a machine learning model may be built as illustrated at steps 520a and 520b. In exemplary aspects, each model built for the type-specific selection is an XGBoost (also referred to as a boosted gradient tree) model. Prior to building the models, randomized features of each type may be created by permuting the features, or rearranging the values. For example, every continuous feature may be permuted such that the features are shuffled to retain the same values but are assigned to different instances. Additionally, a fraction (such as 10%) of the categorical features, chosen at random, may be permuted. Each model may then be built with the regular features and permuted versions. For example, a first model (such as a first XGBoost model) may be built with continuous features and the permuted versions, and a second model (such as a second XGBoost model) may be built with categorical features and the permuted versions.

At steps 530a and 530b, continuous features and categorical features, respectively, may be identified for potential selection. The features may be identified based on satisfying a threshold of importance for predicting pneumonia readmission. In exemplary aspects, for instance, the importance (in terms of gain) of each feature may be calculated for each of the two models. Permuted features may be sorted based on their importance (gain), and the 95th percentile value may be found. The 95th percentile demarcates features with a gain that is higher (or more important) than 95% of all of the permuted features. This calculation of the 95th percentile may be performed separately for the permuted categorical features and the permuted continuous features such that separate 95th percentile values were found for each type of feature. These 95th percentile values may then be used as thresholds for selecting the non-permuted (i.e., original, real) features as potential features for use in the predictor. Accordingly, features with values satisfying the threshold may be selected. In exemplary aspects, this step means that any feature with a gain greater than or equal to these 95th percentile values for their respective feature type (continuous vs. categorical) may be retained from the type-specific model.

Once continuous and categorical features are selected for potential use, sequential modeling may be applied to all potential features (continuous and categorical), as indicated at step 540. Any permuted features that passed the respective threshold may be removed such that the models are applied only to actual features. In some embodiments, one or more severity indices are not part of the previous steps for feature selection. In this case, severity indices that have been withheld may be added back to the pool of potential features at step 540. In other embodiments, the severity indices are all part of the initial feature selection process in steps 510-530, but are added back into the pool of potential features even if these features did not satisfy the importance/gain threshold.

As used herein, sequential modeling refers to applying a plurality of models in a sequence such that the output of at least one model is used in building a subsequent model. In exemplary embodiments, the sequential modeling of step 540 includes three models. A first model may be built for the categorical and continuous features selected in steps 530a and 530b. The coefficients of the features from the first model may then be used to build a second model, and the coefficients for features from the second model may be used in building a third model. The features selected by the third model may be the final features used for the predictive model, such as one of the GLM models in the ensemble discussed with respect to FIG. 4.

In some embodiments, the plurality of models used for the sequential modeling in feature selection is an adaptive GLMnet, where each model is a GLMnet. Because a general linear model is not as sensitive to the distinction between categorical and continuous features compared to a gradient tree model, these models may be run on both types of features together. In applying the sequential models, coefficients from each model may be used to create a vector of penalty factors that are used for building the subsequent GLMnet. In one embodiment actually reduced to practice, the coefficients were selected by finding the lambda value that gives the minimum mean cross-validated error and then selecting the largest lambda that has an error within one standard error of the minimum.

Embodiment Actually Reduced to Practice

In an embodiment actually reduced to practice, the primary pieces of software used were the XGBoost and GLMnet libraries, both available from the CRAN collection of libraries for the R programming language and RStudio development environment. Additional packages included data.table and magrittr (for data management), foreach and doParallel (for parallelizing code), Hmisc and ggplot (for exploratory data analysis), and caret (for identifying rare features).

In building the models, certain criteria was used identify index episodes to be used for the reference dataset. This criteria included:

Episode takes place in 2012 or later;
Patient is age 18 or above;
Has a Pneumonia diagnostic code and either:
   The Pneumonia diagnosis has a priority of Primary; or
   There exists a Sepsis diagnosis with a priority of Primary and there does not exist a Severe Sepsis diagnosis;
Admission source is not a Transfer;
Episode type is not one of the following:
   Home Health/Hospice/LTC/SNF/Nursing Home;
   Outpatient/Clinic/Day Surgery/Outpatient Surgery/Recurring; or
   Non-Patient/Unknown-Invalid/Not Mapped
Discharge is not one of the following:
   Expired/Hospice;
   Null/Not Mapped/Unknown-Invalid;
   Left Against Medical Advice;
   Transfer to Law Enforcement; or
   Transfer to Hospital;
Discharged at least one day after admission (e.g., discharge date minus admission date ≥1);
Does not have a qualifying pneumonia encounter (e.g., one meeting the above criteria) in the 30 days before the index;
At least one prior episode in the previous two years;
One of the following:
   Has a follow-up episode between 30 and 395 days following index; or
   Has an unplanned inpatient episode between 0 and 30 days following index and the patient died or was discharged to hospice at the end of the follow-up episode;
One of the following:
   Does not have an unavoidable inpatient episode between 0 and 30 days following the index; or
   Has an unplanned avoidable inpatient episode before having an unavoidable inpatient episode between 0 and 30 days following the index;
Comes from a hospital and month with one the following property:
   For each hospital and month, consider all potential index episodes (those which passed the above criteria) that occurred during this month and at this hospital;
   For each of these index episodes, check if the episode(s) during their two-year lookback window had at least one medication and at least one procedure;
   Compute the fraction of all episodes for this hospital and month that had at least one medication and at least one procedure; and
   Use only those hospital-month pairings with at least 30 episodes, where over 60% of those episodes had a medication during their lookback window and over 50% of those episodes had a procedure during their lookback window as valid pairings;
Comes from a hospital that was not excluded due to being an outlier with respect to certain features;
Has a hemoglobin test within the current episode;
Has at least one blood urea nitrogen (BUN) test and one systolic blood pressure (SBP) test within the past two years;
   If SBP is missing but Diastolic Blood Pressure and Mean Arterial Pressure are available, SBP is calculated from these and the episode may be included;
The class value (outcome variable) was defined as follows:
   There exists an unplanned inpatient episode (called the "follow-up episode") between 24 hours and 30 days following discharge from the index episode.

Because embodiments uses an ensemble of ten different models trained on slightly different versions of the training data, not all of the features discussed herein were used in every ensemble member. FIG. 6 provides a chart 600 that indicates how frequently each feature appeared in the embodiment actually reduced to practice.

As stated, in some embodiments, the prediction is made using an ensemble of ten logistic regression models, each with their own model coefficients. FIG. 7 illustrates a table 700 that identifies the minimum, maximum, and median values for coefficients across ten models as well as whether or not the coefficient flipped sign in any of the models in an embodiment actually reduced to practice. For all binary features, the coefficient in table 700 is the value added into the model when the feature was present; if the feature was absent, that value was not added.

Figure 8A:
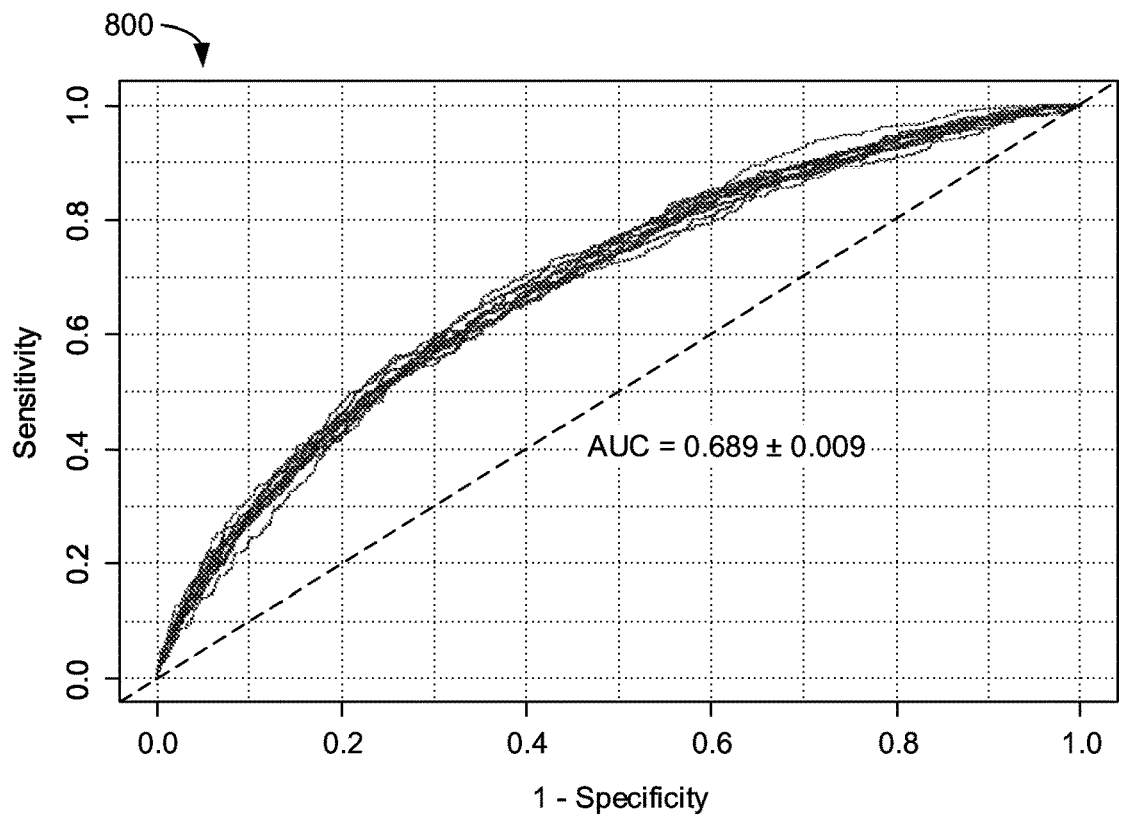
FIGS. 8A-C depict graphical illustrations of the performance of a pneumonia readmission predictor suitable for use within a decision support system and actually reduced to practice.
Figure 8B:
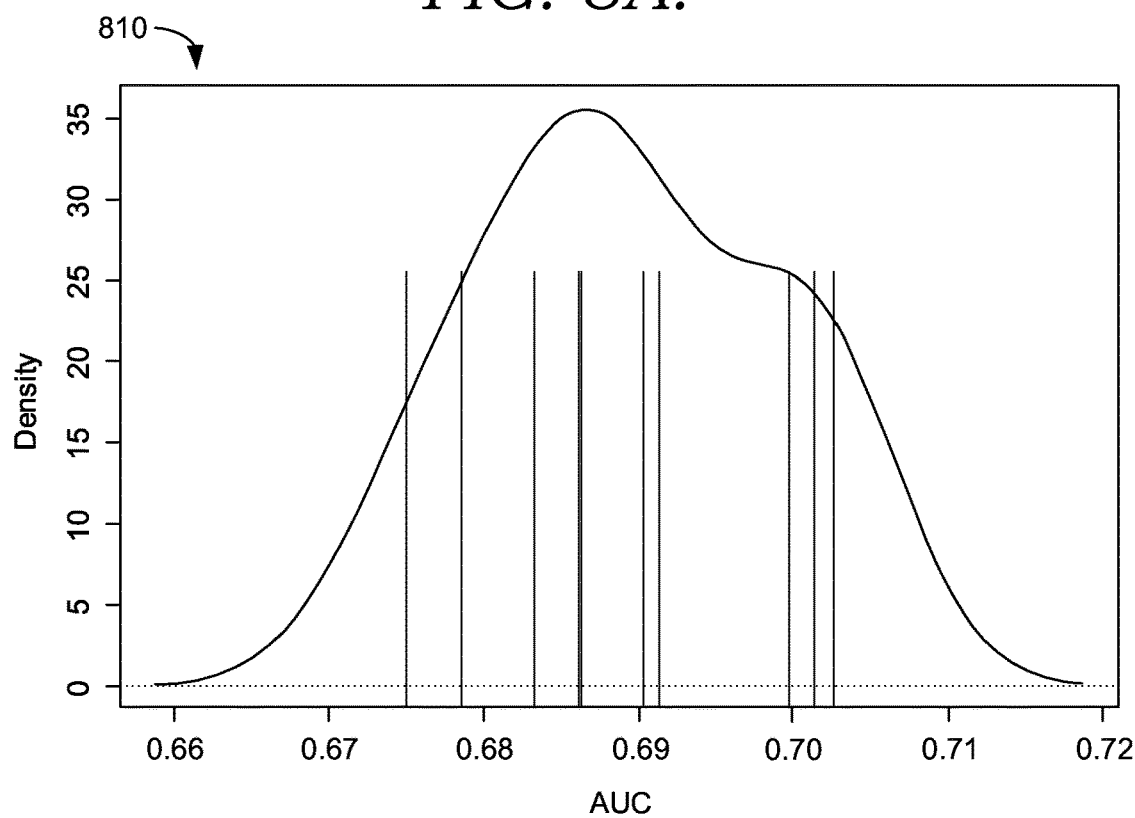
Figure 8C:
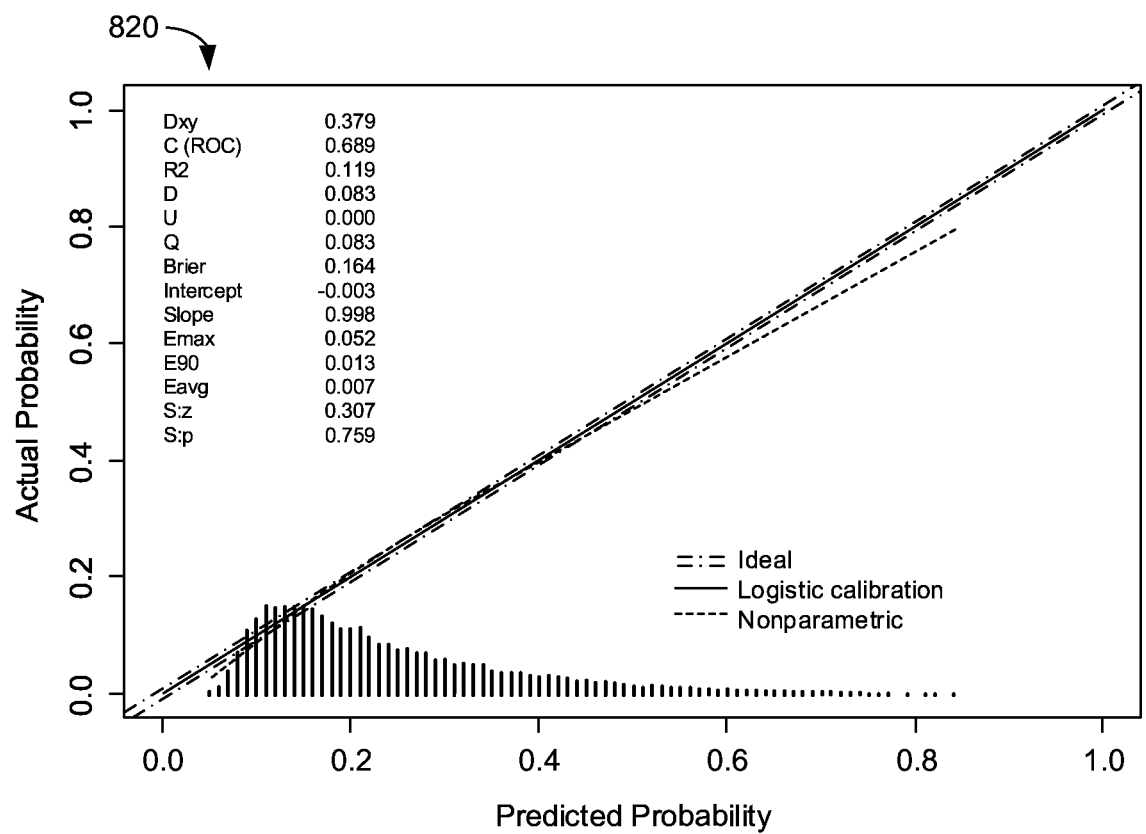

To evaluate the performance of the predictor actually reduced to practice, a 10-fold cross validation was applied, performing the entire feature selection and model-building process (but not the choice of imputation values for the laboratory features) inside the cross-validation. In other words, within each fold of the outer, testing cross-validation process, the entire model-building cross-validation process was performed. Averaging together the AUC (area under the curve) results for each run of testing cross-validation, the overall AUC was 0.689. FIG. 8A depicts ROC (receiver operating characteristic) plots 800 for all ten runs overlaid on top of each other. FIG. 8B depicts a histogram and density plot 810 of all AUC values for the ten runs, which illustrates the variation embodied by the different runs. FIG. 8C illustrates a plot 820 validating the probabilities predicted by the model, demonstrating how the predicted probabilities of each instance compare with the empirical probabilities for instances from a given degree of risk. As illustrated, embodiments of the disclosure improve upon conventional methods at least by yielding fairly accurate predictions of pneumonia readmission prior to discharge such that intervening action may be initiated and instituted to effectuate a reduction in readmissions.

Many different arrangements of the various components depicted, as well as components not shown, are possible without departing from the spirit and scope of the present invention. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Computer storage media having computer-executable instructions embodied thereon that, when executed, provide a method for implementing a decision support tool for pneumonia patients, the method comprising:
receiving patient information for a patient being treated for pneumonia;
applying an ensemble of models to the patient information to generate a prediction of the patient being readmitted for pneumonia within a future time interval, wherein the patient information used to generate the prediction is available prior to discharge of the patient; and
based on the prediction of whether the patient will be readmitted for pneumonia, initiating one or more intervening actions prior to discharge to reduce a likelihood of readmission, the one or more intervening actions performed by automatically modifying computer code executed in a healthcare software program for treating the patient and/or discharging planning, thereby transforming the program at runtime.

2. The computer storage media of claim 1, wherein the prediction is based on one or more severity metrics, each severity metric being computed by the patient information.

3. The computer storage media of claim 2, wherein the one or more severity metrics includes a cancer score indicating whether the patient had a cancer diagnosis within a relevant time frame.

4. The computer storage media of claim 3, wherein the cancer score is computed by assigning a point to each cancer diagnosis and applying a maximum score.

5. The computer storage media of claim 4, wherein one point is assigned for a diagnoses for each of the following: cancer of bronchus, secondary malignancies, gastrointestinal cancer, cancer of lymphatic and hematopoietic tissue, and neoplasms of unspecified nature or uncertain behavior, and wherein one point is assigned for a prescription of maintenance chemotherapy or radiation.

6. The computer storage media of claim 3, wherein a maximum score of three is applied to the cancer score.

7. The computer storage media of claim 2, wherein the one or more severity metrics includes an epilepsy or seizure score indicating whether the patient has a diagnosis of epilepsy or other condition associated with seizures or whether the patient has been prescribed a medication associated with epilepsy or other condition associated with seizures.

8. The computer storage media of claim 2, wherein the one or more severity metrics includes an instability score based on one or more lab result values for the patient, wherein the one or more lab result values indicate a degree of instability.

9. The computer storage media of claim 8, wherein the one or more lab result values include values for one or more of calcium, hematocrit, albumin, bicarbonate, chloride, serum creatinine, and lymphocyte percentage.

10. The computer storage media of claim 1, wherein the ensemble of models comprises a plurality of generalized linear models each generated using a different set of features from reference information, wherein features included within each set of features are selected using one or more gradient boost tree models.

11. A computer system for providing a discharge decision support tool for reducing readmissions due to pneumonia, the system comprising:
one or more processors;
computer storage media storing computer-useable instructions that, when executed by the one or more processors, implement a method comprising:
receiving patient information for a patient being treated for pneumonia;
determining one or more severity metrics for the patient using at least some of the patient information;
applying an ensemble of machine learning models to the patient information and the one or more severity metrics to generate a prediction of the patient being readmitted for pneumonia within a future time interval, wherein the patient information used to generate the prediction is available prior to discharge of the patient; and
based on the prediction of whether the patient will be readmitted for pneumonia, initiating one or more intervening actions to reduce a likelihood of readmission, the one or more intervening actions performed by automatically modifying computer code executed in a healthcare software program for treating the patient and/or discharging planning, thereby transforming the program at runtime.

12. The computer system of claim 11, wherein the future time interval is 30 days.

13. The computer system of claim 11, wherein the one or more intervening actions comprises modifying discharge instructions for the patient.

14. The computer system of claim 11, wherein the one or more intervening actions comprises scheduling a follow up appointment for the patient within the future time interval.

15. The computer system of claim 11, wherein the one or more severity metrics include a cancer score, an epilepsy or seizure score, a pneumococcal pneumonia score, and an instability score based one lab results of the patient.

16. The computer system of claim 11, wherein the ensemble of machine learning models comprises ten linear regression models each utilizing a different set of features as input.

17. A computerized method for providing a discharge decision support tool to reduce pneumonia readmissions, the method comprising:
receiving reference information on a reference population;
selecting a plurality of features for predicting pneumonia readmisison, wherein selecting the plurality of features comprises applying sequential modeling using a plurality of feature-selection models to a potential feature pool based on reference information available prior to discharge;
training a plurality of prediction models to predict a likelihood that a patient will be readmitted with pneumonia within a future time interval, each prediction model being trained on a different set of features from the plurality of features; and
generating a prediction that a target patient will be readmitted with pneumonia within the future time interval using the plurality of prediction models, wherein each prediction model provides a probability and wherein the probabilities from the plurality of prediction models are combined to generate the prediction, wherein the prediction is generated prior to discharge of the target patient; and
based on the prediction of whether the patient will be readmitted for pneumonia, initiating one or more intervening actions to reduce a likelihood of readmission, the one or more intervening actions performed by automatically modifying computer code executed in a healthcare software program for treating the patient and/or discharging planning, thereby transforming the program at runtime.

18. The computerized method of claim 17, wherein selecting the plurality of features further comprises determining the potential feature pool by:
   dividing the reference information into categorical features and continuous features;
   train a first gradient tree model using the categorical features and a second gradient tree model using the continuous features;
   identify potential categorical features from the first gradient tree model and potential continuous features from the second gradient tree model; and
   combine the potential categorical features, the potential continuous features, and one or more severity metrics to create the potential feature pool.

19. The computerized method of claim 17, wherein the plurality of prediction models comprises an ensemble of ten linear regression models and wherein the plurality of feature-selection models comprises an adaptive GLMnet.

20. The computerized method of claim 17, wherein the prediction that the target patient will be readmitted with pneumonia within the future time interval is used to automatically initiate one or more intervening actions to reduce the likelihood of readmission.

\* \* \* \* \*

UNITED STATES PATENT AND TRADEMARK OFFICE
CERTIFICATE OF CORRECTION

PATENT NO. : 11,468,994 B2
APPLICATION NO. : 16/457082
DATED : October 11, 2022
INVENTOR(S) : Randall Wald, Andrew Roberts and Sasanka Are It is certified that error appears in the above-identified patent and that said Letters Patent is hereby corrected as shown below:

In the Drawings

Sheet 7 of 10, Line 25: Delete "Menstraul" and insert -- Menstrual --.
Sheet 8 of 10, Line 19: Delete "Multrum" and insert -- Multum --.
Sheet 8 of 10, Line 36: Delete "Antineopastic" and insert -- Antineoplastic --.

In the Specification

Column 13, Line 19: Delete "predictions" and insert -- predictions. --.
Column 19, Line 10: Delete ""SSNRI" and insert -- "SNRI --.

In the Claims

Column 26, Line 45: In Claim 17, delete "readmisison," and insert -- readmission, --.

Signed and Sealed this
Twenty-fourth Day of January, 2023

Katherine Kelly Vidal
*Director of the United States Patent and Trademark Office*